United States Patent [19]

Sen et al.

[11] Patent Number: 5,510,525

[45] Date of Patent: Apr. 23, 1996

[54] DIRECT CATALYTIC OXIDATIVE CARBONYLATION OF LOWER ALKANES TO ACIDS

[75] Inventors: Ayusman Sen; Minren Lin, both of State College, Pa.

[73] Assignee: Gas Research Institute, Chicago, Ill.

[21] Appl. No.: 357,437

[22] Filed: Dec. 16, 1994

Related U.S. Application Data

[63] Continuation-in-part of Ser. No. 95,945, Jul. 22, 1993, Pat. No. 5,393,922.

[51] Int. Cl.$^6$ ................................................. C07C 51/16
[52] U.S. Cl. ................................................. 562/542
[58] Field of Search .................................... 562/542

[56] References Cited

U.S. PATENT DOCUMENTS

| | | |
|---|---|---|
| 1,916,041 | 6/1933 | Dreyfus . |
| 2,922,809 | 1/1960 | Oberdorfer, Jr. . |
| 2,926,191 | 2/1960 | Lawson-Hall et al. . |
| 3,215,733 | 11/1965 | MacLean et al. . |
| 3,284,492 | 11/1966 | Fremery et al. . |
| 3,876,694 | 4/1975 | Gaenzler et al. . |
| 4,101,450 | 7/1978 | Hwang et al. . |
| 4,414,409 | 11/1983 | Waller . |
| 4,469,886 | 9/1984 | Pesa et al. . |
| 4,494,604 | 1/1985 | Shaw et al. . |
| 4,613,693 | 9/1986 | Ray . |
| 4,665,213 | 5/1987 | Alper et al. . |
| 4,681,707 | 7/1987 | Alper et al. . |
| 4,681,751 | 7/1987 | Gosser . |
| 4,739,107 | 4/1988 | Drent . |
| 4,814,538 | 3/1989 | Devries et al. . |
| 4,895,682 | 1/1990 | Ellis, Jr. et al. . |
| 4,996,357 | 2/1991 | Kojima et al. . |
| 5,024,984 | 6/1991 | Kaminsky et al. . |
| 5,087,786 | 2/1992 | Nubel et al. . |
| 5,220,080 | 6/1993 | Lyons et al. . |
| 5,233,113 | 8/1993 | Periana et al. . |
| 5,258,549 | 11/1993 | Pimblett . |
| 5,281,752 | 1/1994 | Fujiwara et al. . |
| 5,286,900 | 2/1994 | Hansen et al. . |

OTHER PUBLICATIONS

Baerns, M., van der Wiele, K., and Ross, J. R. H., Methane Activation—A Bibliography, Catal. Today, 4, 471–474, (1989).

Pitchai, R. and Klier, K., Partial Oxidation of Methane, Catal. Rev.-Sci. Eng., 28(1), 13–88, (1986).

Hunter, N. R., Gesser, H. D., Morton, L. A. Yarlagadda, P. S., and Fung, D. P. C., Methanol Formation at High Pressure by the Catalyzed Oxidation of Natural Gas and by the Sensitized Oxidation of Methane, Appl. Catal., 57, 45–54, (1990).

Burch, R., Squire, G. D., Tsang, S. C., Direct Conversion of Methane into Methanol, J. Chem. Soc., Faraday Trans. 1, 85(10), 3561–3568, (1989).

Kowalak, S. and Moffat, J. B., Partial Oxidation of Methane Catalyzed by H-Mordenite and Fluorinated Mordenite, Appl. Catal., 36, 139–145, (1988).

Stolarov, I. P., Vargaftik, M. N., Shishkin, D. I., and Moiseev, I. I., Oxidation of Ethane and Propane With Co(II) Catalyst, J. Chem. Soc., Commun., 938–939, (1991).

Vargaftik, M. N., Stolarov, I. P., and Moiseev, I. I., Highly Selective Partial Oxidation of Methane to Methyl Trifluoroacetate, J. Chem. Soc., Chem. Commun., 1049–1050, (1990).

Herron, N., The Selective Partial Oxidation of Alkanes Using Zeolite Based Catalysts, New J. Chem., 13, 761–766, (1989).

Lyons, J. E., Ellis, Jr., P. E., and Durante, V. A., Active Iron Oxo Centers for the Selective Oxidation of Alkanes, Stud. Surf. Sci. Catal., 67, 99–116, (1991).

Periana, R. A., Taube, D. J., Evitt, E. R., Loffler, D. G., Wentrcek, P. R., Voss, G. and Masuda, T., A Mercury–Catalyzed, High–Yield System for the Oxidation of Methane to Methanol, Science, 259, pp. 340–343, (1993).

Horvath, I. T., Cook, R. A., Millar, J. M. and Kiss, G., Low–Temperature Methane Chlorination with Aqueous Platinum Chlorides in the Pressence of Chlorine, Organometallics, 12, pp. 8–10, (1993).

Merzouki, M., Taouk, B., Monceaux, L., Bordes, E. and Courtine, P., Catalytic Properties of Promoted Vanadium Oxide in the Oxidation of Ethane in Acetic Acid, New Developments in Selective Oxidation by Heterogeneous Catalysis; Studies in Surface Science and Catalysis, Ruiz, P. and Delmon, B., Eds., vol. 72, pp. 165–179, (1992).

Thomas, C. L., Catalytic Processes and Proven Catalysts, Academic, New York, 104, (1970).

Happel, J., Study of Knietic Structure Using Marked Atoms, Catal. Rev., 6, (2), 221–260, (1972).

Laine, R. M., and Wilson, Jr., R. B., Recent Developments in the Homogeneous Catalysis of the Water–Gas Shift Reaction, in Aspects of Homogeneous Catalysis, Ugo, R., Ed., D. Reidel, Dordrecht, 5, 217–240, (1984).

Ford, P. C., The Water Gas Shift Reaction: Homogeneous Catalysis by Ruthenium and Other Metal Carbonyls, Acc. Chem. Res., 14, 2, 31–37, (1981).

Fu, L., Chuang, K. T. and Fiedorow, R., Selective Oxidation of Hydrogen to Hydrogen Peroxide, New Developments in Selective Oxidation by Heterogeneous Catalysis; Studies in Surface Science and Catalysis, Ruiz, P. and Delmon, B., Eds., vol. 72, pp. 33–41, (1992).

Nicoletti, J. W. and Whitesides, G. M., Liquid–Phase Oxidation of 2–Propanol to Acetone by Dioxygen Using Supported Platinum Catalysts, J. Phys., Chem., 93, 759–767, (1989).

(List continued on next page.)

*Primary Examiner*—José G. Dees
*Assistant Examiner*—Joseph M. Conrad, III
*Attorney, Agent, or Firm*—Speckman, Pauley & Fejer

[57] ABSTRACT

A process for direct oxidative carbonylation of lower alkanes to acids having one greater carbon atom. The process uses a metal salt catalyst promoted by halide ions and/or a metal with oxygen as the oxidant in an aqueous medium. The process is especially effective for conversion of methane to acetic acid.

20 Claims, 2 Drawing Sheets

OTHER PUBLICATIONS

Sen, A. and Lin, M., A Novel Hybrid System for the Direct Oxidation of Ethane to Acetic and Glycolic Acids in Aqueous Medium, J. Chem. Soc., Chem. Commun., 6, 508–510, (1992).

Sen, A., Lin, M., Kao, L. C., and Hutson, A. C., J. Am. Chem. Soc. 114, 6385, (1992).

Jones, W. D., Development of Catalytic Processes for the Synthesis of Organic Compounds the Involve C–H Bond Activation, Chap. 5, 113–148, Selective Hydrocarbond Activation, Principles and Progress, Edited by Davies, J. A., Watson, P. L., Greenberg, A. and Lichman, J. F., VCH, (1990).

Lin, M. and Sen, A., A Highly Catalytic System for the Direct Oxidation of Lower Alkanes by Dioxygen in Aqueous Medium. A Formal Heterogeneous Analog of Alkane Monooxtgenases, J. Am. Chem. Soc., 114, 7307–7308, (1992).

Kunai, A, Wani, T, Uehara, Y, Iwasaki, Kuroda, Y, Ito, S, and Sasaki, K., Catalytic Oxidation of Benzene. Catalyst Design and Its Performance, Bull. Chem. Soc. Jpn., 62, 2613–2617, (1989).

Kuroda, Y., Kunaai, A., Hamada, M., Kitano, T., Ito, S. and Sasaki, K., Catalytic Oxidation of Naphthalene on Palladium in Cooperation with Copper (I)/(II) Redox Couple, Bull. Chem. Soc. Jpn., 64, 3089–3093, (1991).

Groh, S. E. and Nelson, M. J., Mechanisms of Activation of Carbon–Hydrogen Bonds by Metalloenzymes, Chap. 10, 305–378, in Selective Hydrocarbon Activation, Davies, J. A., Watson, P. L., Liebman, J. F., Greenberg, A., Eds. VCH, New York, (1990).

Ortiz de Montellano, P. R., Oxygen Activation and Transfer, Chap. 7, 217–271, in Cytochrome P–450: Structure, Mechanism and Biochemistry, Ortiz de Montellano, P. R., Ed., Plenum, New York, (1986).

Guengerich, F. P. and MacDonald, T. L., Chemical Mechanisms of Catalysis by Cytochromes P–450: A Unified View, Acc. Chem. Res., 17, 9–16, (1984).

Groves, J. T., Key Elements of the Chemistry of Ctochrome P–450, J. Chem. Ed., 62, 11, 928–931, (1985).

Walling, C., Fenton's Reagent Revisited, Acc. Chem. Res. 8, 125–131, (1975).

Bakak, A. and Espenson, J. H., Kinetics of the Capture of Methyl Radicals by Carbon Monoxide in Aqueous Solution, J. Chem. Soc., Chem. Commun., 21, 1497–1498, (1991).

Lin, M. and Sen, A., Oxidation and Oxidative Carbonylation of Methane and Ethane by Hexaoxo–µ–peroxodifulfate (2–) Ion in Aqueous Medium, J. Chem. Soc., Chem. Commun. 12, 892–893, (1992).

Kung, H. H., Selective Oxidation Catalysis II, Stud. Surf. Sci. Catal., 45, 200–226, (1989).

Nishiguchi, T., Nakata, K., Takaki, K. and Fujiwara, Y. Chem. Lett., 1141–1142, (1992).

Lin, M. and Sen, A., J. Chem. Soc., Chem. Commun., 892–893 (1992).

Lin, M. and Sen, A., J. Am. Chem. Soc., 114, 7307–7308, 1992.

Wade, L. E., Gengelbach, R. B., Trumbley, J. L., Kirk–Othmer Encyclopedia of Chemical Technology, vol. 15, 398–415, Wiley, New York (1978).

Wagner, F. S., Kirk–Othmer Encyclopedia of Chemical Technology, vol. 1, 124–147, Wiley, New York (1978).

Forster, D., Adv. Organomet, Chem, 17, 255–267, (1979).

Whitesides, G. M., et al., Organometallics 4, 1819–1830, (1985).

Sen, A., Lin, M., Kao, L–C & Hutson, A. C., *J. Am. Chem. Soc.* 114, 6385–6392 (1992).

Luinstra, G. A., Labinger, J. A., Bercaw, J. E., *J. Am. Chem. Soc.* 115, 3004–3005 (1993).

Kushch, L. A., Lavrushko, V. V., Misharin, Yu. S., Moravsky, A. P. & Shilov, A. E. Nouv. J. Chem. 7, 729–733 (1983).

Lin, M., Sen, Ayusman, Direct catalytic conversion of methane to acetic acid in an aqueous medium, Letters To Nature vol. 368, 613–615 (1994).

DIRECT CATALYTIC OXIDATIVE CARBONYLATION OF LOWER ALKANES TO ACIDS

CROSS REFERENCE TO RELATED APPLICATION

This application is a continuation-in-part application of application Ser. No. 08/095,945, filed Jul. 22, 1993, now U.S. Pat. No. 5,393,922.

BACKGROUND OF THE INVENTION

1. Field of the Invention

This invention relates to a process for the direct oxidative carbonylation of lower alkanes to acids having one greater carbon atom than the alkane. The process proceeds under mild conditions in aqueous media using oxygen as the oxidant. The process is especially effective for the conversion of methane to acetic acid. The process of this invention is carried out under mild temperature conditions involving the reaction of a lower alkane, carbon monoxide and oxygen in aqueous media with a metal salt catalyst promoted by halide ions and/or a metal to produce acid having one more carbon atom than the reactant alkane.

2. Description of Related Art

A number of processes for oxidation of unsaturated hydrocarbons are known, for example: U.S. Pat. No. 3,284,492 teaching oxidation of a ozone-organic compound adduct in an aqueous alkaline hydrogen peroxide solution to produce, from olefins having terminal unsaturation, formic acid plus the acid having one less carbon atom than the original alkene; U.S. Pat. No. 4,739,107 teaching reaction of an unsaturated hydrocarbon, alcohol and CO over Pd or Pt at 20° to 200° C. with $O_2$ optionally present, to form dicarboxylate esters; U.S. Pat. Nos. 4,681,707 and 4,665,213 teaching similar reactions as the 4,739,107 patent with the additional requirement of the catalyst including copper, and teaching substitution of water for the alcohol reactant to produce the corresponding carboxylic acids; U.S. Pat. No. 4,414,409 teaching reaction of an unsaturated hydrocarbon, carbon monoxide and a hydroxylic compound in the presence of a catalyst of an organic phosphine liganded palladium compound and perfluorosulfonic acid to produce corresponding acids and esters; U.S. Pat. No. 3,876,694 teaching oxycarbonylation of olefins to form corresponding acids in a nonaqueous medium using. a catalyst system of aluminum, boron or an alkaline earth metal and a compound of palladium which is soluble in the reaction medium; and U.S. Pat. No. 4,469,886 teaching hydrocarboxylation of propylene with carbon monoxide and water to produce isobutyric acid using a catalyst of palladium, a phosphoamine promoter ligand compound and a hydrogen halide.

Catalytic oxidation of saturated hydrocarbons, such as alkanes, requiring C—H activation is a very different and difficult chemical challenge, and one of great practical importance. The lower alkanes of 1 to about 6 carbon atoms are most abundant and least reactive of the alkanes, with methane being the most abundant and least reactive, having a C—H bond energy of 104 kcal/mol, with ethane being second in both categories. A number of processes have been described for such oxidations but they each suffer from requirement of high temperature and/or low turnovers of less than about 10: Baerns, M., van der Wiele, K., and Ross, J. R. H., Methane Activation—A Bibliography, Catal. Today, 4, 471–494, (1989); Pitchai, R. and Klier, K., Partial Oxidation of Methane, Catal. Rev.-Sci. Eng., 28(1), 13–88, (1986); Kung, H. H., Selective Oxidation Catalysis II, Stud. Surf. Sci. Catal., 45, 200–226, (1989); Hunter, N. R., Gesser, H. D., Morton, L. A., Yarlagadda, P. S., and Fung, D. P. C., Methanol Formation at High Pressure by the Catalyzed Oxidation of Natural Gas and by the Sensitized Oxidation of Methane, Appl. Catal., 57, 45–54, (1990); Burch, R., Squire, G. D., Tsang, S. C., Direct Conversion of Methane into Methanol, J. Chem. Soc., Faraday Trans. 1, 85(10), 3561–3568, (1989); Kowalak, S. and Moffat, J. B., Partial Oxidation of Methane Catalyzed by H-Mordenite and Fluorinated Mordenite, Appl. Catal., 36, 139–145, (1988); Stolarov, I. P., Vargaftik, M. N., Shishkin, D. I., and Moiseev, I. I., Oxidation of Ethane and Propane With Co(II) Catalyst, J. Chem. Soc., Chem. Commun., 938–939, (1991); Vargaftik, M. N., Stolarov, I. P., and Moiseev, I. I., Highly Selective Partial Oxidation of Methane to Methyl Trifluoroacetate, J. Chem. Soc., Chem. Commun., 1049–1050, (1990); Herron, N., The Selective Partial Oxidation of Alkanes Using Zeolite Based Catalysts, New J. Chem., 13, 761–766, (1989); and Lyons, J. E., Ellis, Jr., P. E., and Durante, V. A., Active Iron Oxo Centers for the Selective Oxidation of Alkanes, Stud. Surf. Sci. Catal., 67, 99–116, (1991). The Lyons, et al reference, supra, strives to achieve a one-step route to oxidation of lower alkanes to alcohols using iron oxo complexes as catalysts. The oxidation of lower alkanes with $O_2$ catalyzed by azide-activated Group IV(a) to VIII transition metal coordination complexes is taught by U.S. Pat. No. 4,895,682. One well known disadvantage of such coordination complexes is their tendency to degrade under oxidative conditions. Mercury catalyzed oxidation of methane to methanol under mild conditions is taught by Periana, R. A., Taube, D. J., Evitt, E. R., Loffler, D. G., Wentrcek, P. R., Voss, G. and Masuda, T., A Mercury-Catalyzed, High-Yield System for the Oxidation of Methane to Methanol, Science, 259, pp. 340–343, (1993). U.S. Pat. No. 5,220,080 teaches direct catalytic oxidation of light alkanes to alcohols using a catalyst in which chromium is chemically bound to oxygen of a metal oxide support surface. Low temperature reaction of methane with chlorine in the presence of platinum chlorides and in-situ hydrolyzation of the formed methyl chloride to methanol is taught by Horvath, I. T., Cook, R. A., Millar, J. M. and Kiss, G., Low-Temperature Methane Chlorination with Aqueous Platinum Chlorides in the Presence of Chlorine, Organometallics, 12, pp. 8–10, (1993). Catalytic oxidation of ethane to acetic acid at temperatures above about 250° C. using promoted vanadium oxide catalysts is taught by Merzouki, M., Taouk, B., Monceaux, L., Bordes, E. and Courtine, P., Catalytic Properties of Promoted Vanadium Oxide in the Oxidation of Ethane in Acetic Acid, New Developments in Selective Oxidation by Heterogeneous Catalysis; Studies in Surface Science and Catalysis, Ruiz, P and Delmon, B., Eds., Vol. 72, pp. 165–179, (1992). Conversion of lower alkanes into their corresponding esters by contact with an oxidizing agent, a strong mineral acid, and a catalyst comprising a Group VIII noble metal is taught by U.S. Pat. No. 5,233,113.

Metal catalyzed oxidation of alcohol to carboxylic acid requiring a divalent platinum complex for the initial oxidation step is taught by Sen, A. and Lin, M., A Novel Hybrid System for the Direct Oxidation of Ethane to Acetic and Glycolic Acids in Aqueous Medium, J. Chem. Soc., Chem. Commun., 6, 508–510, (1992) and Sen, A., Lin, M., Kao, L. C., and Hutson, A. C., J. Am. Chem. Soc. 114, 6385, (1992).

The partial oxidation of methane in a motored engine at 650° to 800° C. and under compression of 20/1 to 60/1 without any catalyst to form small amounts of oxygenated products is taught by U.S. Pat. No. 2,922,809.

Non-catalytic oxidation of a paraffin hydrocarbon of 4 to 8 carbon atoms in the liquid phase with molecular oxygen to produce lower aliphatic acids of 1 to 4 carbon atoms is taught by U.S. Pat. No. 2,926,191.

The formation of acetic acid from methane and carbon dioxide and the formation of acetaldehyde from methane and carbon monoxide by addition reactions in the presence of a metal catalyst, such as palladium or platinum or their carbonates, is taught by U.S. Pat. No. 1,916,041. It must be noted that there is no net oxidation in the reactions taught by the 1,916,041 patent. Further, the addition reactions referred to in U.S. Pat. No. 1,916,041 are thermodynamically uphill and cannot proceed except to produce trace amounts of the products as set forth by Jones, W. D., Development of Catalytic Processes for the Synthesis of Organic Compounds the Involve C—H Bond Activation, Chap. 5, 113–148, Selective Hydrocarbon Activation, Principles and Progress, Edited by Davies, J. A., Watson, P. L., Greenberg, A. and Lichman, J. F., VCH, (1990).

Methane is the most abundant of the alkanes, but is the least reactive, making its use as a reactant to produce more useful chemical products difficult to achieve. The industrial production of acetic acid from methane involves many steps under extreme reaction conditions. Wade, L. E., Gengelbach, R. B., Trumbley, J. L. and Hallbauer, W. L., Kirk-Othmer Encyclopedia of Chemical Technology, Vol. 15, 398–415, Wiley, New York (1978); Wagner, F. S., Kirk-Othmer Encyclopedia of Chemical Technology, Vol. 1. 124–147, Wiley, New York (1978); and Forster, D., Adv. Organomet, Chem, 17, 255–267, (1979). Reports of direct catalytic conversion of methane to acetic acid have involved use of peroxydisulphate as the oxidant. Nishiguchi, T., Nakata, K., Takaki, K. and Fujiwara, Y., Chem. Lett., 1141–1142, (1992) and Lin, M. and Sen, A., J. Chem. Soc., Chem. Commun., 892–893 (1992). Conversion of methane to acetic acid on a commercial scale currently involves three separate steps: (1) high-temperature steam reforming of methane to a 3:1 mixture of $H_2$ and CO as taught by Wade et al, supra; (2) high-temperature conversion of a 2:1 mixture of $H_2$ and CO to methanol as taught by Wade, et al, supra; and (3) carbonylation of methanol to acetic acid as taught by Wagner, supra, mainly through the Monsanto process as taught by Forster, supra. Carbonylation of methanol to acetic acid using a rhodium catalyst and an iodide promoter is taught by U.S. Pat. Nos. 5,258,549 and 5,286,900 and other processes for production of acetic acid are taught by U.S. Pat. Nos. 4,101,450; 4,613,693; 4,996,357; and 5,281,752. Conversion of methane to higher hydrocarbons is taught by U.S. Pat. Nos. 4,814,538; 5,024,984; and 5,087,786.

Our prior U.S. patent application, Ser. No. 08/095,945, filed Jul. 22, 1993, now allowed, and the article by Lin, M. and Sen, A., J. Am. Chem. Soc., 114, 7307–7308, 1992 describe the direct oxidation of lower alkanes by hydrogen peroxide in an aqueous medium with metallic palladium on carbon alone as a catalyst results in the oxidation of lower alkanes to their corresponding acid, such as methane primarily to formic acid.

SUMMARY OF THE INVENTION

It is an object of this invention to provide a process for direct catalytic oxidative carbonylation of lower alkanes to acids using $O_2$ as the oxidant under mild reaction conditions in an aqueous medium.

Another object of this invention is to provide a process for direct catalytic oxidative carbonylation of lower alkanes to acids having one greater carbon atom than the alkane reactant, particularly methane to selectively produce principally acetic acid, at temperatures below about 200° C.

Yet another object of this invention is to provide a process for direct catalytic oxidative carbonylation of lower alkanes to acids, particularly methane to acetic acid, using a catalyst system of a soluble metal salt catalyst and halide ions and/or a metal promoter.

The process of this invention involves the direct catalytic oxidative carbonylation of a lower alkane to a carboxylic acid having one greater carbon atom under mild conditions using oxygen as the oxidant in an aqueous containing system. The process may be described as the reaction of a mixture of alkane, CO and $O_2$ in the presence of a metal salt catalyst and a promoter in an aqueous medium with mild heating according to the reaction:

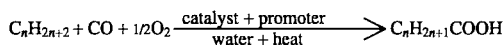

$$C_nH_{2n+2} + CO + 1/2O_2 \xrightarrow[\text{water + heat}]{\text{catalyst + promoter}} C_nH_{2n+1}COOH$$

wherein n=1 to about 6.

BRIEF DESCRIPTION OF THE DRAWINGS

Further advantages of the invention will be apparent upon reading of preferred embodiments and reference to the drawings wherein.

DESCRIPTION OF PREFERRED EMBODIMENTS

Figures 1, 1A:
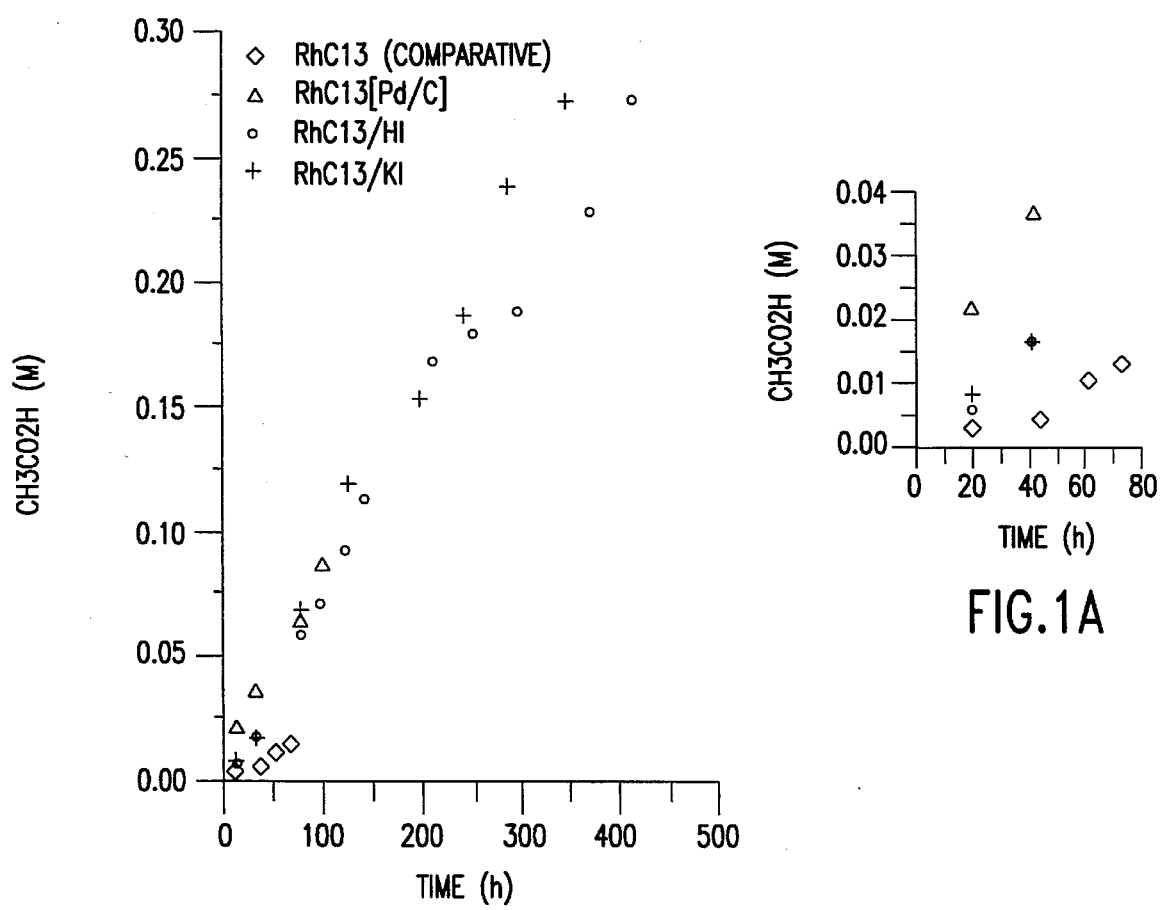
FIGS. 1 and 1A are graphs showing production of acetic acid as a function of time using a catalyst and promoter according to the process of this invention compared to using solely a catalyst.

The process of this invention involves the direct catalytic oxidative carbonylation under mild temperature conditions of lower alkanes to acids having one more carbon atom than the alkane reactant. Suitable alkane reactants include those having 1 to about 6 carbon atoms, straight and branched chain, namely methane, ethane, propane, isopropane, butane, isobutane, pentane, isopentane, hexane, isohexane, and other branched and cyclic alkanes of up to about 6 carbon atoms. The alkane reactants need not be pure, but may include mixtures of lower alkanes such as found in natural gas. The process of this invention is especially effective and selective for production of acetic acid when using methane as the reactant alkane.

Suitable metal salt catalysts for use in the direct catalytic carbonylation of alkanes according to this invention include salts of Fe, Ru, Os, Co, Rh, Ir, Ni, Pd, Pt, Cu, Ag, Au and mixtures thereof which may be used as soluble salts or on a suitable support. It is preferred to use metal salts, such as chlorides, which are soluble in the aqueous reaction medium. To obtain the selective carbonylation desired in the process of this invention, it is necessary to use a promoter in addition to the metal salt catalyst. Suitable promoters are halide ions, selected from iodide, bromide and chloride ions and metallic metals selected from Fe, Ru, Os, Co, Rh, Ir, Ni, Pd, Pt, Cu, Ag, Au and mixtures of halide ions, metallic metals or halide ions and metallic metals. The halide ions may be provided by a suitable source and the metallic metal promoter may be used on a support, such as carbon, or directly in the reaction medium in high surface area metallic form. At least one of the catalyst and the promoter must be soluble in the aqueous reaction medium. Both the catalyst and the promoter may be soluble in the aqueous reaction medium. Preferred catalysts are Rh, Ir, Pd and Ru and preferred promoters are halides. A particularly preferred system is use of $RhCl_3$ as the catalyst and a halide as the promoter. The catalyst and promoter are suitably present in molar proportions of catalyst:promoter of 1:about 4 to 75 and preferably 1:about 4 to 15.

While an aqueous medium is necessary for conduct of the process of this invention, the terminology is meant to include pure water and solvent mixtures in which water is a component. Reaction medium mixtures of water and a solvent in which one of the components of reaction has a larger solubility may be used, such as a 6:1 mixture of perfluorinated acid and water. We have found higher reaction rates using 6:1 mixtures of perfluorobutyric acid and water in which methane has a higher solubility.

Carbon monoxide and dioxygen are supplied to the reaction in gaseous form, such as by bubbling into the aqueous reaction medium under pressure. While a wide range of amounts of these gases work, it is preferred that the CO be supplied in excess of the $O_2$, a preferred molar ratio of $CO:O_2$ is about 3:1. When the alkane reactant is in gaseous phase, it may be introduced into the aqueous medium under pressure, with higher rates of reaction with higher alkane pressure. When the alkane reactant is in the liquid phase, it may be added to the aqueous reaction medium and well stirred. It is preferred to carry out the reaction at a pH of 7 or lower.

The reaction may be carried out at temperatures of about 50° to about 200° C., preferably about 80° to about 160° C.

The reaction may be carried out in a batch or in a continuous mode using vessels and process equipment which will be familiar to one skilled in the art upon understanding the desired conditions for conduct of the process of this invention.

In one preferred embodiment of the invention, methane is reacted with a mixture of carbon monoxide and oxygen in the presence of the metal catalyst salt $RhCl_3$ dissolved in water in the presence of a halide promoter to form principally acetic acid. Formic acid and methanol were the only significant by-products observed in the solution. No product was observed if either CO or $O_2$ was omitted from the reaction mixture. The selectivity and yield of acetic acid was substantially increased upon the addition of a source of halogen ion, such as $I^-$, or a metal, such as 5% metallic Pd on carbon promoter. We have run the methane oxidative carbonylation reaction to produce acetic acid with $RhCl_3$ catalyst (0.01M)+HCl in 5 ml $D_2O$ in 125 ml glass lined steel reactors under conditions set forth in Table 1. The product yields were determined by $^1H$-NMR spectroscopy.

TABLE 1

| Promoter | $H^+$(M) | $Cl^-$ (M) | Temp. (°C.) | Time (Hr) | Yields (M) (mmol in parenthesis) $CH_3CO_2H$ | $CH_3OH$ | $HCO_2H$ |
|---|---|---|---|---|---|---|---|
| None* | 0.1 | 0.13 | 140 | 60 | 0.012 (0.060) | 0.0052 (0.026) | 0.0176 (0.088) |
|  |  |  |  | 72 | 0.014 (0.070) | 0.0050 (0.025) | 0.0252 (0.126) |
| Pd/C*+ | 0.1 | 0.13 | 150 | 88 | 0.066 (0.330) | 0.0040 (0.020) | 0.0372 (0.186) |
|  |  |  |  | 108 | 0.088 (0.440) | 0.0046 (0.023) | 0.0592 (0.296) |
| HI** (0.025M) | 0.125 | 0.13 | 95 | 88 | 0.064 (0.320) | trace (trace) | trace (trace) |
|  |  |  |  | 130 | 0.092 (0.460) | trace (trace) | 0.0020 (0.010) |
|  |  |  |  | 420 | 0.276 (1.380) | trace (trace) | 0.0100 (0.050) |
| KI** (0.025M) | 0.0005 | 0.13# | 95 | 88 | 0.070 (0.350) | trace (trace) | 0.0168 (0.084) |
|  |  |  |  | 132 | 0.120 (0.600) | trace (trace) | 0.0366 (0.183) |
|  |  |  |  | 248 | 0.188 (0.940) | 0.0020 (0.010) | 0.0340 (0.170) |
|  |  |  |  | 352 | 0.275 (1.375) | 0.0065 (0.0325) | 0.105 (0.525) |

*$CH_4$ (800 psi); CO (200 psi); $O_2$ (100 psi).
+5% Pd on C (10 mg) 60 μmol surface Pd atoms per gm catalyst determined by $H_2$ chemisorption.
**$CH_4$ (1,000 psi); CO (150 psi); $O_2$ (50 psi).
NaCl added instead of HCl.

FIGS. 1 and 1A are graphs showing production of acetic acid from methane as a function of time under the conditions set forth in Table 1 with the FIG. 1A graph being an expansion showing the first 80 hours of the reactions. It is seen that formic acid and methanol were the only significant by-products observed in the reaction solution. No product was observed if either CO or $O_2$ was omitted from the reaction mixture. The yield of acetic acid was substantially increased by addition of a promoter and there was no significant decrease in catalytic activity, even after more than 400 hours of reaction time. As taught by the parent application and Lin, M. and Sen, A., J. Am. Chem. Soc., 114, 7307–7308, (1992), when metallic palladium on carbon is used as the sole catalyst methane undergoes straightforward oxidation to form principally formic acid rather than acetic acid. Only formic acid was observed when 5% metallic rhodium on carbon alone was substituted for $RhCl_3$. Also the addition of mercury, which would be expected to amalgamate and remove any colloidal rhodium present (Whitesides, G. M., et al, Organometallics 4, 1819–1830, (1985), had no significant effect upon the rate during the first 20 hours, longer reaction times resulted in gradual removal of all soluble rhodium species due to reduction by mercury metal. These observations are consistent with a soluble rhodium species rather than a metallic rhodium being the active catalyst for acetic acid formation. In the absence of added $Cl^-$ ions, lower rates were observed.

A catalyst system of a mixture of $RhCl_3$ and $I^-$ ions has some similarity to the 'Monsanto' system for carbonylation of methanol to acetic acid (Forster, D., Adv. Organomet. Chem., supra) wherein the active species is $[Rh(CO_2)I_2]^-$. The important differences are that in the Monsanto system: no oxidant is used and there is no net oxidation; a higher temperature is generally used; and a substantially lower pressure CO is used. In the present reaction system, a somewhat higher pressure of CO was required to prevent catalyst degradation. A separate experiment showed that in that absence of added CO, the Rh(I)—carbonyl species present in the reaction system were decomposed by $O_2$.

Figure 2:
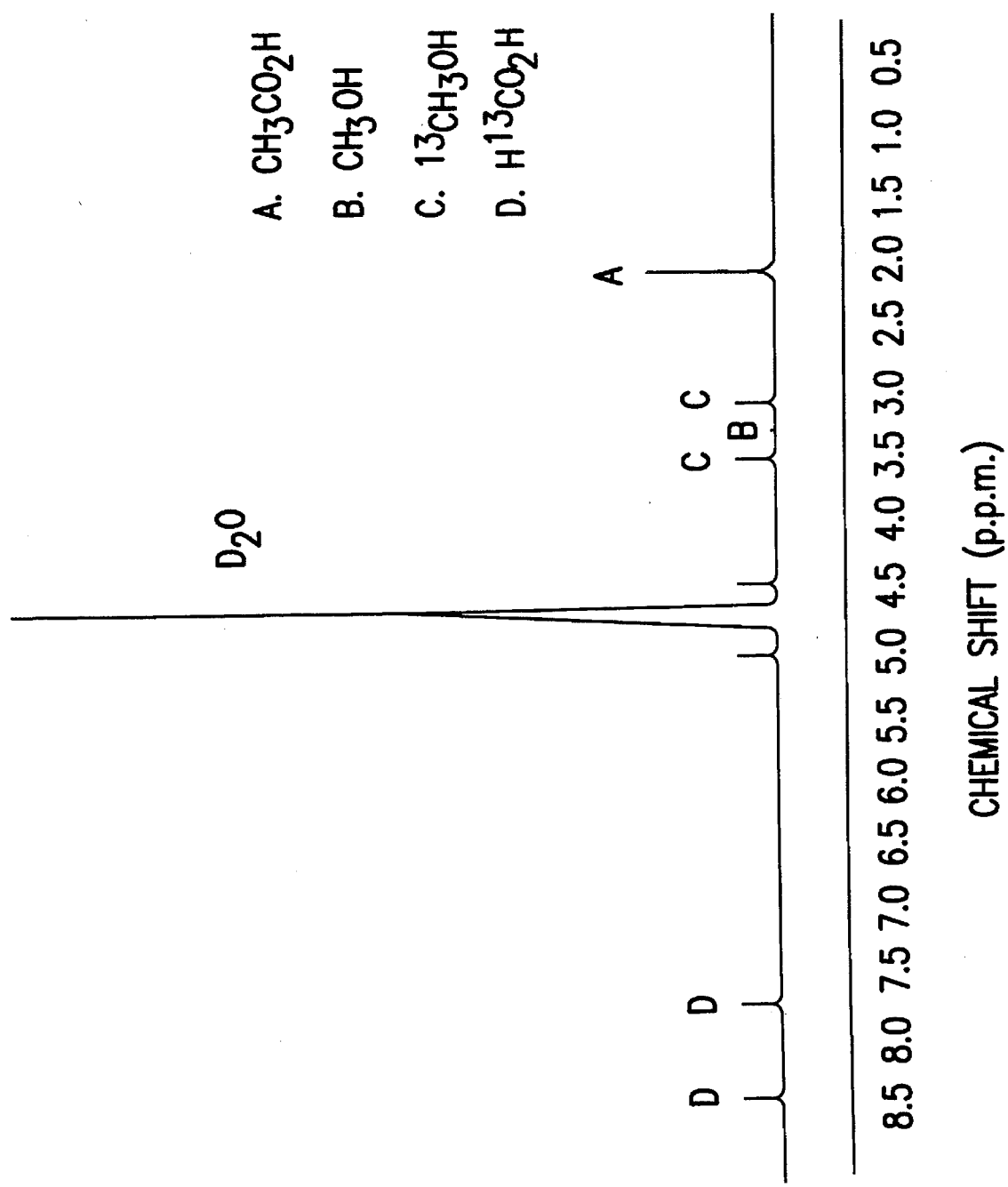
FIG. 2 is a $^1$H-NMR spectrum of products obtained according to one embodiment of the process of this invention.

In the Monsanto system, a $Rh-CH_3$ species is formed initially from methanol by way of methyl iodide which is subsequently carbonylated to a $Rh-C(O)CH_3$ species and then hydrolyzed to acetic acid. In the direct catalytic oxidative carbonylation of the present invention, the conversion of methane to acetic acid does not proceed through the intermediacy of methanol. We have examined the products formed after reaction at 100° C. for 20 hours of a system of $RhCl_3$ (0.01M), HI (0.01M), $CH_4$ (1,100 psi, 0.06M in water), $^{13}CH_3OH$ (0.06M), CO(200 psi), $O_2$ (50 psi), and $D_2O$ (5 mil). FIG. 2 shows a $^1$H-NMR spectrum of the products obtained showing chemical shifts with respect to HDO at 4.67 ppm. For both the $RhCl_3$ and $RhCl_3+I^-$ systems, only $CH_4$ was converted to acetic acid while $^{13}CH_3OH$ was simply oxidized to $H^{13}CO_2H$. This clearly indicates that the formation of the $Rh-CH_3$ species from methane occurred at a substantially faster rate than that from methanol. The methanol and its oxidized product, formic acid, formed in the system of this invention presumably arose through the hydrolysis of a fraction of the $Rh-CH_3$ species formed from methane. Since the back reaction, formation of $Rh-CH_3$ from methanol, did not occur, the product distribution indicated that the hydrolysis rate was substantially slower that the rate of carbonylation to the corresponding $Rh-C(O)CH_3$ species. Since methanol was not carbonylated to acetic acid under the reaction system of the present invention, the function of the promoter halogen ion cannot be the same as in the Monsanto system.

When using alkanes higher than methane in the process of this invention, the conversion rate was found to be significantly faster, but the desired product specificity was lower. We have found that using ethane the rate of hydrolysis of the $Rh-C_2H_5$ intermediate was comparable to the carbonylation rate, and thus acetic acid was derived from ethanol through a subsequent oxidation.

The following examples are set forth in detail with respect to specific materials and reaction conditions to more clearly demonstrate the invention and should not be considered to limit the invention in any manner.

EXAMPLE I

The catalytic oxidative carbonylation of methane to selectively produce high yields of acetic acid was carried out in a 125 ml glass lined stainless steel bomb which was maintained at 95° C. $CH_4$ at 800 psi, CO at 150 psi, and $O_2$ at 50 psi were added the bomb which contained a solution of $RhCl_3$ (0.01M), HCl (0.1M), and HI (0.025M) in 5 ml $D_2O$.

The reaction was allowed to proceed for the times indicated and products determined by $^1$H NMR spectroscopy as shown in Table 2.

TABLE 2

| Time (Hours) | Products (mmol) | | |
|---|---|---|---|
| | $CH_3CO_2H$ | $CH_3OH$ | $HCO_2H$ |
| 20 | 0.036 | — | — |
| 40 | 0.090 | — | — |
| 88 | 0.315 | — | trace |
| 106 | 0.365 | trace | trace |
| 130 | 0.460 | trace | trace |
| 150 | 0.572 | trace | 0.059 |
| 216 | 0.850 | trace | 0.120 |
| 260 | 0.904 | trace | 0.125 |
| 304 | 0.954 | trace | 0.125 |
| 376 | 1.160 | trace | 0.230 |
| 420 | 1.380 | trace | 0.240 |

Table 2 shows the high selectivity of the process of this invention for production of acetic acid from methane.

EXAMPLE II

The process was conducted as described in Example I except that the temperature was maintained at 110° C. The reaction was allowed to proceed for the times indicated and the products determined as shown in Table 3.

TABLE 3

| Time (Hours) | Products (mmol) | | |
|---|---|---|---|
| | $CH_3CO_2H$ | $CH_3OH$ | $HCO_2H$ |
| 24 | 0.040 | 0.018 | trace |
| 68 | 0.097 | 0.012 | trace |
| 88 | 0.123 | 0.016 | 0.038 |

EXAMPLE III

The process was conducted as described in Example I except that HCl was omitted and the reaction allowed to proceed for the times indicated and products determined as shown in Table 4.

TABLE 4

| Time (Hours) | Products (mmol) | | |
|---|---|---|---|
| | $CH_3CO_2H$ | $CH_3OH$ | $HCO_2H$ |
| 20 | 0.043 | trace | trace |
| 40 | 0.085 | trace | trace |
| 88 | 0.200 | trace | trace |
| 106 | 0.237 | trace | trace |

EXAMPLE IV

The process was conducted as described in Example I except that 10 mg of 5% palladium on carbon was used instead of HI. The process was conducted for the times and at the temperatures indicated and products determined as shown in Table 5.

TABLE 5

| Temp. (°C.) | Time (Hours) | Products (mmol) | | |
|---|---|---|---|---|
| | | $CH_3CO_2H$ | $CH_3OH$ | $HCO_2H$ |
| 95 | 20 | 0.076 | 0.014 | 0.008 |
| 120 | 20 | 0.055 | 0.007 | 0.006 |
| 120 | 40 | 0.073 | 0.010 | 0.007 |
| 150 | 20 | 0.115 | 0.018 | 0.003 |
| 150 | 40 | 0.189 | 0.021 | 0.077 |
| 150 | 88 | 0.330 | 0.020 | 0.092 |
| 150 | 108 | 0.440 | 0.023 | 0.143 |
| 165 | 48 | 0.141 | 0.015 | 0.035 |
| 165 | 68 | 0.102 | 0.023 | 0.161 |
| 165 | 88 | 0.094 | 0.026 | 0.230 |

EXAMPLE V

The process was conducted as described in Example I except NaCl (0.1M) was used instead of HCl (0.1M), KI (0.025M) was used instead of HI (0.025M), and HCl was added to maintain the solution pH at about 3. The process was conducted for the times indicated and products determined as shown in Table 6.

TABLE 6

| Time (Hours) | Products (mmol) | | |
|---|---|---|---|
| | $CH_3CO_2H$ | $CH_3OH$ | $HCO_2H$ |
| 20 | 0.046 | trace | trace |
| 40 | 0.090 | trace | trace |
| 88 | 0.346 | trace | 0.042 |
| 132 | 0.600 | trace | 0.090 |
| 204 | 0.773 | trace | 0.090 |
| 248 | 0.942 | trace | 0.100 |
| 292 | 1.210 | 0.039 | 0.172 |
| 352 | 1.370 | 0.033 | 0.265 |
| 396 | 1.550 | 0.034 | 0.385 |

EXAMPLE VI

The process was conducted as described in Example V except that 21.5 mg $K_3RuCl_6$ (0.05 mmol) was used instead of $RhCl_3$ (0.01M). The process was conducted for the times and at the temperatures indicated and products determined as shown in Table 7

TABLE 7

| Temp. (°C.) | Time Hours | Products (mmol) | | |
|---|---|---|---|---|
| | | $CH_3CO_2H$ | $CH_3OH$ | $HCO_2H$ |
| 95 | 18 | 0.0035 | 0.0025 | trace |
| 95 | 58 | 0.0060 | trace | trace |
| 125 | 20 | 0.0080 | 0.0030 | 0.0080 |

EXAMPLE VII

The process was conducted as described in Example V except that 15 mg of $IrCl_3$ (0.05 mmol) was used instead of $RhCl_3$ (0.01M). The process was conducted for the times and at the temperatures indicated and products determined as shown in Table 8.

TABLE 8

| Temp. (°C.) | Time (Hours) | Products (mmol) | | |
|---|---|---|---|---|
| | | $CH_3CO_2H$ | $CH_3OH$ | $HCO_2H$ |
| 95 | 18 | 0.0065 | trace | trace |
| 95 | 86 | 0.0060 | 0.0060 | trace |
| 125 | 20 | 0.0050 | 0.0050 | trace |

EXAMPLE VIII

The process was conducted as described in Example V except that $CH_3CH_3$ (550 psi) was used instead of $CH_4$ (800 psi) and the temperature was maintained at 95° C. The process was conducted for the times indicated and products determined as shown in Table 9.

TABLE 9

| Time (Hours) | Products (mmol) | | | |
|---|---|---|---|---|
| | $C_2H_5CO_2H$ | $CH_3CO_2H$ | $CH_3CH_2OH$ | $HCO_2O$ |
| 20 | 0.063 | 0.031 | 0.032 | — |
| 40 | 0.140 | 0.115 | 0.057 | — |
| 84 | 0.225 | 0.370 | 0.067 | 0.039 |
| 128 | 0.310 | 0.825 | 0.075 | 0.082 |
| 196 | 0.310 | 1.450 | 0.088 | 0.184 |

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

We claim:

1. A process for direct catalytic oxidative carbonylation of lower alkanes to acids having one greater carbon atom than said lower alkane, comprising: contacting said lower alkane with carbon monoxide and oxygen in an aqueous medium and in the presence of a metal salt catalyst wherein said metal is selected from the group consisting of Fe, Ru, Os, Co, Rh, Ir, Ni, Pd, Pt, Cu, Ag, Au and mixtures thereof and a promoter selected from the group consisting of iodide, bromide and chloride ions, metallic metals Fe, Ru, Os, Co, Rh, Ir, Ni, Pd, Pt, Cu, Ag, Au, and mixtures thereof.

2. A process according to claim 1 wherein said metal salt catalyst comprises a metal selected from the group consisting of Rh, Ir, Pd and Ru.

3. A process according to claim 2 wherein said salt is chloride.

4. A process according to claim 1 wherein said promoter is a halide ion selected from the group consisting of iodide, bromide, chloride ions and mixtures thereof.

5. A process according to claim 1 wherein said promoter is a metallic metal selected from the group consisting of Fe, Ru, Os, Co, Rh, Ir, Ni, Pd, Pt, Cu, Ag, Au and mixtures thereof.

6. A process according to claim 5 wherein said promoter is in the reaction medium in metallic form.

7. A process according to claim 5 wherein said promoter is on a catalyst support.

8. A process according to claim 1 wherein said catalyst is $RhCl_3$ and said promoter is an ion selected from the group consisting of iodide, bromide, chloride and mixtures thereof.

9. A process according to claim 1 wherein said contacting is performed at about 50° to about 200° C.

10. A process according to claim 1 wherein said contacting is performed at about 80° to about 160° C.

11. A process according to claim 1 wherein said carbon monoxide is present in an excess molar amount to said oxygen.

12. A process according to claim 1 wherein said aqueous medium is water.

13. A process according to claim 1 wherein said aqueous medium comprises water and a solvent in which said alkane has a greater solubility.

14. A process according to claim 13 wherein said aqueous medium comprises water and perfluorinated acid.

15. A process according to claim 1 wherein said lower alkane has 1 to about 6 carbon atoms and is selected from the group consisting of straight chain, branched chain and cyclic configurations.

16. A process according to claim 1 wherein said lower alkane is principally methane to produce principally acetic acid.

17. A process for direct catalytic oxidative carbonylation of lower alkane comprising principally methane to acids comprising principally acetic acid, comprising: contacting said lower alkane with carbon monoxide and oxygen in an aqueous medium in the presence of (1) a metal salt catalyst soluble in said aqueous medium wherein said metal comprises a metal selected from the group consisting of Rh, Ir, Pd, Ru and mixtures thereof and (2) a promoter selected from the group consisting of iodide, bromide, chloride ions and mixtures thereof, said contacting performed at temperatures of about 50° to about 200° C.

18. A process according to claim 17 wherein said salt is chloride.

19. A process according to claim 17 wherein said aqueous medium comprises water and a solvent in which said alkane has greater solubility.

20. A process for conversion of methane to acetic acid comprising: contacting methane with carbon monoxide and oxygen in an aqueous medium in the presence of $RhCl_3$ catalyst and a promoter selected from the group consisting of iodide, bromide, chloride ions and mixtures thereof at temperature of about 80° to about 160° C., said carbon monoxide being supplied in excess of said oxygen on a molar basis.

* * * * *